(12) United States Patent
Sandblom

(10) Patent No.: US 8,781,688 B2
(45) Date of Patent: Jul. 15, 2014

(54) METHOD AND SYSTEM FOR COMBINING SENSOR DATA

(75) Inventor: Fredrik Sandblom, Göteborg (SE)

(73) Assignee: Volvo Lastvagnar AB, Göteborg (SE)

( * ) Notice: Subject to any disclaimer, the term of this patent is extended or adjusted under 35 U.S.C. 154(b) by 360 days.

(21) Appl. No.: 13/127,983

(22) PCT Filed: Nov. 7, 2008

(86) PCT No.: PCT/SE2008/000634
§ 371 (c)(1), (2), (4) Date: Aug. 9, 2011

(87) PCT Pub. No.: WO2010/053410
PCT Pub. Date: May 14, 2010

(65) Prior Publication Data
US 2012/0083974 A1   Apr. 5, 2012

(51) Int. Cl.
*B60W 30/00* (2006.01)

(52) U.S. Cl.
USPC ............ 701/45; 701/1; 701/47; 701/301; 340/435; 340/436; 340/439; 340/576; 340/903

(58) Field of Classification Search
CPC ..... B60W 30/00; B60W 40/06; B60W 50/00; G01S 7/00
USPC .......... 701/1, 45, 47, 301; 340/435, 436, 439, 340/576, 903
See application file for complete search history.

(56) References Cited

U.S. PATENT DOCUMENTS

| 5,482,314 | A | * | 1/1996 | Corrado et al. | 280/735 |
|---|---|---|---|---|---|
| 5,521,580 | A | | 5/1996 | Kaneko et al. | |
| 6,026,340 | A | * | 2/2000 | Corrado et al. | 701/47 |
| 6,580,973 | B2 | * | 6/2003 | Leivian et al. | 701/1 |
| 6,909,947 | B2 | * | 6/2005 | Douros et al. | 701/34.4 |
| 6,922,632 | B2 | * | 7/2005 | Foxlin | 701/517 |
| 6,925,425 | B2 | * | 8/2005 | Remboski et al. | 702/188 |
| 7,124,027 | B1 | | 10/2006 | Ernst, Jr. et al. | |

(Continued)

FOREIGN PATENT DOCUMENTS

| DE | 102005014803 A1 | 10/2006 |
|---|---|---|
| EP | 1484014 A1 | 12/2004 |
| EP | 1878604 A1 | 1/2008 |
| EP | 1897773 A1 | 3/2008 |

OTHER PUBLICATIONS

Tatschke, T., "Early sensor data fusion techniques for collision mitigation purposes", Proceedings of IV2006, IEEE Intelligent Vehicles Symposium, Jun. 13-15, 2006.

(Continued)

*Primary Examiner* — John R Olszewski
*Assistant Examiner* — Truc M Do
(74) *Attorney, Agent, or Firm* — WRB-IP LLP

(57) ABSTRACT

A method is provided for combining sensor data collected by at least two sensors coupled to at least one application, wherein at least one of the sensors provides driver-related sensor data of a driver-related behavior and at least one external sensor provides sensor date not related to driver-related behavior. The sensor data of the at least two sensors are combined as the respective measurement errors of the data are uncorrelated in time with respect to the at least one application.

15 Claims, 8 Drawing Sheets

(56) References Cited

U.S. PATENT DOCUMENTS

| | | | |
|---|---|---|---|
| 7,565,230 B2* | 7/2009 | Gardner et al. | 701/32.7 |
| 7,579,942 B2* | 8/2009 | Kalik | 340/435 |
| 7,725,253 B2* | 5/2010 | Foxlin | 701/519 |
| 7,831,407 B2* | 11/2010 | Huang et al. | 702/141 |
| 7,920,102 B2* | 4/2011 | Breed | 345/7 |
| 8,009,025 B2* | 8/2011 | Engstrom et al. | 340/438 |
| 8,170,725 B2* | 5/2012 | Chin et al. | 701/1 |
| 8,384,534 B2* | 2/2013 | James et al. | 340/439 |
| 2002/0091473 A1* | 7/2002 | Gardner et al. | 701/35 |
| 2002/0116156 A1* | 8/2002 | Remboski et al. | 702/188 |
| 2002/0120374 A1* | 8/2002 | Douros et al. | 701/29 |
| 2004/0239509 A1* | 12/2004 | Kisacanin et al. | 340/575 |
| 2006/0027404 A1* | 2/2006 | Foxlin | 178/18.06 |
| 2006/0251293 A1* | 11/2006 | Piirainen et al. | 382/104 |
| 2006/0284839 A1* | 12/2006 | Breed et al. | 345/156 |
| 2006/0287779 A1* | 12/2006 | Smith et al. | 701/1 |
| 2007/0057781 A1* | 3/2007 | Breed | 340/457.1 |
| 2007/0073473 A1 | 3/2007 | Altan et al. | |
| 2007/0075919 A1* | 4/2007 | Breed | 345/8 |
| 2008/0084283 A1* | 4/2008 | Kalik | 340/435 |
| 2008/0085686 A1* | 4/2008 | Kalik | 455/154.1 |
| 2008/0154438 A1* | 6/2008 | Kalik | 701/1 |
| 2010/0019880 A1* | 1/2010 | Huang et al. | 340/5.1 |
| 2010/0253526 A1* | 10/2010 | Szczerba et al. | 340/576 |
| 2010/0253539 A1* | 10/2010 | Seder et al. | 340/903 |
| 2011/0153276 A1* | 6/2011 | Lee et al. | 702/188 |
| 2011/0169625 A1* | 7/2011 | James et al. | 340/439 |

OTHER PUBLICATIONS

International Search Report for corresponding International Application PCT/SE2008/000634.

International Preliminary Report on Patentability for corresponding International Application PCT/SE2008/000634.

\* cited by examiner

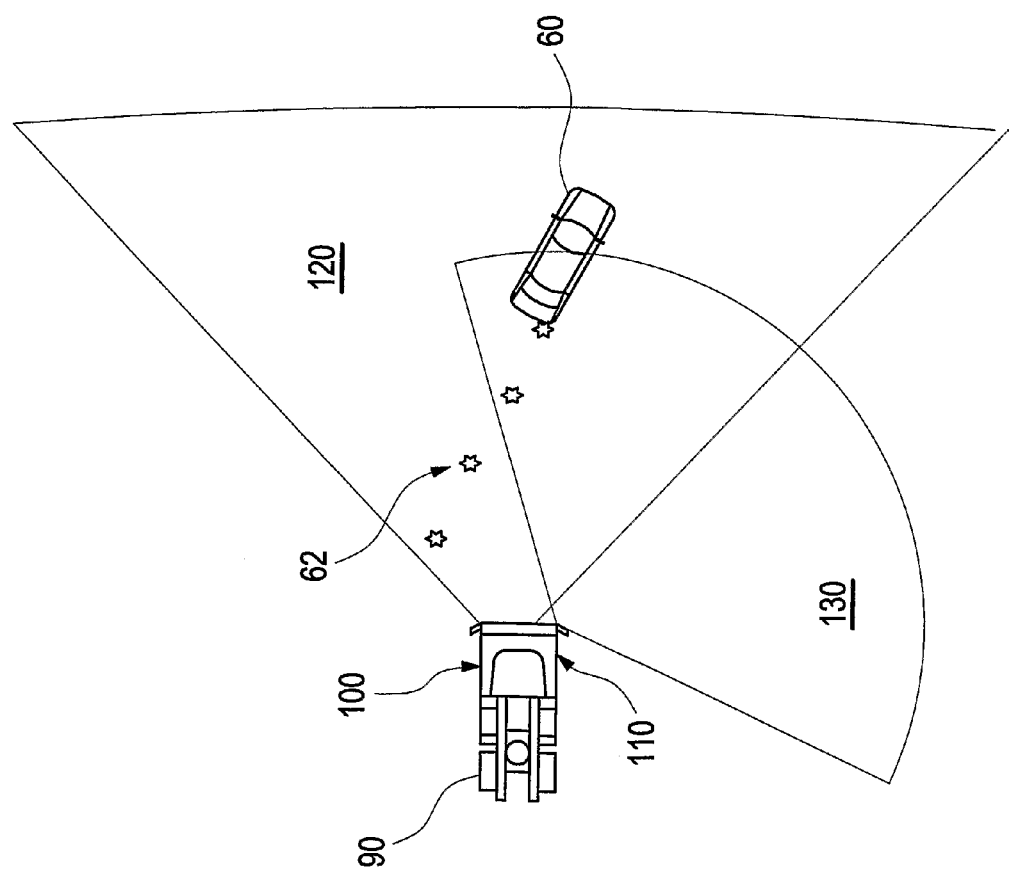

METHOD AND SYSTEM FOR COMBINING SENSOR DATA

The invention relates to a method and a system for combining sensor data.

Modern vehicles can be equipped with sensors for detecting driver gaze orientation and the like. Such information is used for instance to assess driver distraction and fatigue of drowsiness. It is also known in the art to provide sensors for monitoring the vehicle's surrounding traffic situation. The information collected by these sensors is for instance supplied to applications like collision warning systems which are used to prevent or mitigate collisions between the vehicle and an obstacle.

A safety system which has to quickly and appropriately react on a threat must be aware of the threat. This information is supplied by a tracking system using data from sensors monitoring the surrounding environment. For this reason it is desirable that tracks of a probable obstacle are initiated and reported to a safety system as early as possible. It is also desirable that a track that is reported is assigned a high track score. A track score is a quantity that assesses how much one can trust the reported track. In general, a track is reported as valid to safety application when a certain track score has been reached.

This can be achieved in the art by acquiring several consecutive measurements and hence is time consuming. The time needed is proportional to the quality of the measurements. A general rule is the more and better measurements are the shorter validation period is needed.

The track score is maintained after validation and is dynamically updated to reflect the quality of the score at any time. A property of a tracking system that performs well is high track scores.

Achieving high track scores can be assessed by building detailed sensor models, improving present sensors or adding multiple sensors, also known as sensor fusion.

EP 1 878 602 A1 discloses a safety system for a vehicle where a driver alert is issued based on the proportion of off-road gaze time and the duration of a current off-road gaze. The system incorporates driver focus/driver attention as a sensor capable of generating measurements. The ocular state of the driver is detected and compared to data from sensors that monitor the surrounding environment. The system can conclude if the driver has the focus on an impending danger or if the driver is non-attentive.

It is desirable to provide a method and a system which improves reliability and/or speed of data assessment of data collected by sensors A method is proposed for combining sensor data collected by at least two sensors coupled to at least one application, wherein at least one of the sensors provides driver-related sensor data of a driver-related behaviour and at least one external sensor provides sensor date not related to driver-related behaviour. The sensor data of the at least two sensors are combined as the respective measurement errors of the data are uncorrelated in time with respect to the at least one application. In general data from two sensors are not uncorrelated. On the contrary, e.g. if two sensors are both viewing the same object, data is naturally correlated, as it represents the same physical object. However, the measurement errors are usually modeled as uncorrelated, which is often a very good assumption, e.g. for sensors using different measurement principles.

Advantageously, the driver is modelled as an additional sensor ("driver sensor") providing driver-related sensor data, achieved by using an additional sensor that monitors the driver. Particularly, the driver-related data indicate parameters such as a gaze direction, a head orientation and/or any other orientation of the driver indicating a gaze direction and/or a driver attention (awareness) with respect to an object in the surrounding ambient. The driver information can be used to identify objects in cluttered environments and/or be used to prepare a tracking system to see an object that may enter the field of view of a traditional (external) sensor. By incorporating driver focus/driver attention as a sensor capable of generating measurements, by way of example a safety system can perform better and act quicker. The safety system can also provide information whether a driver is aware if a particular target or not. According to prior art, sensor data are combined in a far later stage, particularly, the output of sensor fusion is combined with the output of the driver-related sensor.

According to an advantageous method step, the sensor data of the at least two sensors can be preferably combined in a state where noise of the sensor data is uncorrelated in time. The early fusion of the sensor data allows for considering the driver-related data as raw data as anyone of other sensor data.

According to a further advantageous method step, the sensor data of the at least two sensors can be fed to a sensor fusion unit for combination and/or exchange of the sensor data. The information of the driver-related sensor data can be shared with other sensor data before the data is fed to a concrete application. The analysis of sensor data can become more accurate and faster.

According to a further advantageous method step, the sensor data can be transmitted to one or more applications subsequent to the sensor fusion unit, wherein noise of the sensor data is correlated in time after processing in the sensor fusion unit. The application can preferably be an assistant function applied in a vehicle, such as a tracking system, a safety system, e.g. collision warning and the like.

According to a further advantageous method step, the sensor data can be pre-processed before fed into the sensor fusion unit, enabling a more accurate and more sensitive analysis of the sensor data.

According to a further advantageous method step, driver-related sensor data can comprise at least driver attention and/or driver gaze direction data. This is particularly favourable if the fused sensor data are presented to a tracking system or a safety system such as a collision warning system.

According to a further advantageous method step, the driver-related sensor data and data derived from the application can be used to estimate the driver's field of view. Favourably, the individual driver's field of view can be entered into a threat assessment algorithm (a threat assessment issue is mentioned in the invention disclosure) which subsequently can assess if a possible danger detected by one or more external sensors can be realized by the driver. Further, validation of a track of an object can be improved and can happen faster than in the prior art.

According to a further advantageous method step, a reaction time of the driver and/or a distraction level of the driver can be derived from a comparison between driver-related sensor data indicating cognitive detection of an object and detection of the object by the at least one external sensor. The comparison can most likely be dependent of other things as well, e.g. the driver field of view. Favourably, if the reaction time is long, an alarm, e.g. when there is a risk of a collision, can be issued earlier and when the reaction time is short, an alarm van be issued later. This reduces the risk of false alarms which might irritate and distract the driver. Further, if a vehicle is used by a multitude of drivers, individual driver profiles can be stored and the applications coupled to assist functions can be adapted to the individual driver. Particularly, the profiles can include the driver field of view.

According to a further advantageous method step, a reaction time can be extracted from a time difference between a detection of an object by the at least one external sensor and driver-related sensor data indicating cognitive detection of the same object by the driver. Particularly, the reaction time can be monitored over a predetermined time span yielding an estimate on the driver attention. For instance, an increase in the reaction time of the driver can be interpreted as a reduction of driver attention, and an appropriate warning and/or reaction of the application can be issued. The reaction time can also be dependent on the driver field of view, which can also be taken into account.

According to a further advantageous method step, the at least one application can be a vehicular safety system.

According to a further advantageous method step, the reaction time of one or more drivers can be extracted and stored for use in the vehicular safety system. Safety functions can be adapted to individual drivers.

According to a further advantageous method step, the reaction time can particularly be used to adapt a sensitivity level of the safety system. In contradistinction to the invention, it is difficult to design the sensitivity of an active safety system in prior art. If a safety system is too sensitive, it will suffer from a high false alarm rate. If the safety system is insensitive it might be too late to act when a decision is taken. If the reaction time can be estimated and compared to a general driver profile, particularly a fixed profile or an adaptive profile, estimated during suitable driving scenarios, for instance, a safety system can be designed to warn earlier or later than for a case where no information regarding the driver reaction time is available, thus increasing the performance of the safety system. Particularly, due to latencies in sensor systems and limited sensor coverage, estimation of a reaction time by using tracks may not be sufficient. Typically, when tracks are reported, these data are old and their age is usually unknown.

According to a further advantageous method step, the reaction time can be used to evaluate a level of driver attention. If the reaction time changes within a predetermined time, particularly increases, an alarm can be issued. It is not necessary to verify how the driver handles the vehicle but rather if the driver is much better or worse at assessing the environment than the external sensors, such as radar, lidar, cameras and the like, employed in or coupled to the vehicle.

According to a further advantageous method step, the at least one application can be a tracking system. By modelling the driver as a sensor it can be derived early, if a driver recognizes an oncoming object and a probable danger or not. Also, information regarding object properties such as position, size, perceived interest can be extracted.

According to a further advantageous method step, the driver-related sensor data can be combined with tracking data of one or more objects, making the analysis more accurate and faster. Particularly, a track can be validated with higher reliability and probably earlier than with purely external sensors.

According to a further advantageous method step, in a tracking system a sensor model can be built which at least comprises one or more of
(i) a probability that the driver notices one or more object;
(ii) an accuracy of a driver monitoring camera presenting a driver's head and/or gaze direction;
(iii) a relation between head/gaze direction and position of one or more objects viewed by the driver;
(iv) a probability that the driver looks at non-objects;
(v) an impact on track confidence as a function of driver attention.

According to a further advantageous method step, a track can be recognized as valid if tracking sensor data and driver-related sensor data coincide.

According to another aspect of the invention, a safety system is proposed which employs a method for combining sensor data collected by at least two sensors coupled to at least one application, wherein at least one of the sensors provides driver-related sensor data of a driver-related behaviour and at least one external sensor provides sensor data not related to driver-related behaviour, wherein the sensor data of the at least two sensors are combined as the respective measurement errors of the date are uncorrelated in time with respect to the at least one application. Favourably, the invention can be a component in a tracking system. The safety system can be e.g. a collision warning system, a cruise control system and the like for instance collision avoidance system, intersection safety system, lane change assist system, and preferably any system that needs to know where other objects are.

According to another aspect of the invention, a tracking system is proposed which employs a method for combining sensor data collected by at least two sensors coupled to at least one application, wherein at least one of the sensors provides driver-related sensor data of a driver-related behaviour and at least one external sensor provides sensor date not related to driver-related behaviour, wherein the sensor data of the at least two sensors are combined as the respective measurement errors of the data are uncorrelated in time with respect to the at least one application, wherein the system comprises at least one of a tracking system and a safety system.

Further, a computer program comprising a computer program code adapted to perform a method or for use in a method for combining sensor data collected by at least two sensors coupled to at least one application, wherein at least one of the sensors provides driver-related sensor data of a driver-related behaviour and at least one external sensor provides sensor date not related to driver-related behaviour, wherein the sensor data of the at least two sensors are combined as the respective measurement errors of the data are uncorrelated in time with respect to the at least one application when said program is run on a programmable microcomputer. Preferably, the computer program can be adapted to be downloaded to a control unit or one of its components when run on a computer which is connected to the internet.

Further, a computer program product stored on a computer readable medium is proposed, comprising a program code for use in a method on a computer, wherein the method is a method for combining sensor data collected by at least two sensors coupled to at least one application, wherein at least one of the sensors provides driver-related sensor data of a driver-related behaviour and at least one external sensor provides sensor date not related to driver-related behaviour, wherein the sensor data of the at least two sensors are combined as the respective measurement errors of the data are uncorrelated in time with respect to the at least one application.

BRIEF DESCRIPTION OF THE DRAWINGS

The present invention together with the above-mentioned and other objects and advantages may best be understood from the following detailed description of the embodiments, but not restricted to the embodiments, wherein is shown schematically:

FIG. 8 an example where an obstacle is first detected by a driver sensor and validation is not influenced by an external sensor at this first stage.

DETAILED DESCRIPTION

Figure 1:
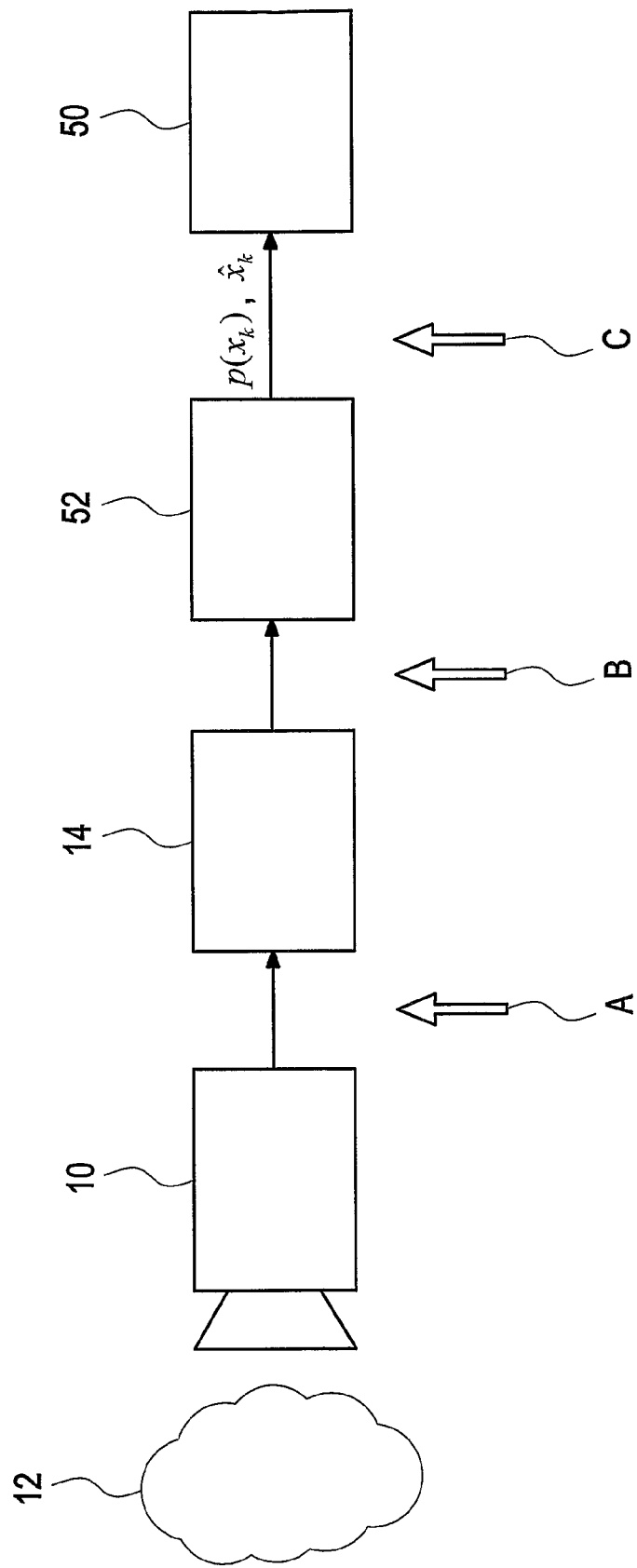
FIG. 1 according to a preferred embodiment of the invention radar data levels, e.g. raw data, detection instances and tracks.

In the drawings, equal or similar elements are referred to by equal reference numerals. The drawings are merely schematic representations, not intended to portray specific parameters of the invention. Moreover, the drawings are intended to depict only typical embodiments of the invention and therefore should not be considered as limiting the scope of the invention.

Particularly, when the invention is used in combination with a tracking filter, the invention may be treated as an extension of the tracking filter. Favourably, according to the invention, a new sensor such as the driver sensor can be included and correctly treated, preferably as a component in a tracking framework. The invention can then provide as benefits a decreased validation time, a driver time statistic and more.

According to a preferred embodiment of the invention, FIG. 1 depicts schematically a preferred way how data are produced and presented to an application 50 via a tracking system 52, originating from radar data levels of, e.g. raw data, detection instances and tracks. A radar sensor 10 monitors an ambient 12. For a radar sensor 10 measurements consist of or comprise detections B. the radar sensor 10 sends raw data A as input to a unit 14. The unit 14 provides a signal detection algorithm, that for example can be based on spectral analysis using Fourier transformation to detect objects. The output of unit 14 comprises detections B which are fed into the application 52, e.g. a collision mitigation system or the like.

The detections B originate from signal peaks which are determined by detection algorithms to originate from an object in the radar field of view, e.g. which are thresholded, i.e. are above a predefined or adaptively set signal level. Properties of such detections are e.g. a range, an azimuth and a velocity of a detected object in the radar field of view. The tracking system 52 outputs tracks C in form of an estimate of a position $\hat{x}_k$ and/or expected values of a position $E[x_k]$ and/or a probability density function $p(x_k)$ of its state vector $x_k$. It should be noted that this position can be multidimensional to include velocities and the like. The data C are presented to an application 50.

Particularly, detections B are positions in measurement space of objects visible to the radar sensor 10, but no time correlation is assumed. That is, the detection algorithms do not make use of earlier detections when detecting a new one. In contradistinction to this, the tracking system 52 makes use of an earlier detection when a new detection B is detected.

The detections output by the tracking system 52 are detections verified through time and model consistency.

A state vector $x_k$ describes an environment 12 surrounding the vehicle carrying a sensor i (e.g. radar sensor 10 mounted on a vehicle) at time $t_k=kT_s$, for a system with a constant sample time $T_s$. Because measurements generally are influenced by stochastic noise, $x_k$ is a stochastic parameter and is described through its probability density function $p(x_k)$.

$y_k^i$ describes the measurements presented by sensor i at time $t_k$. As they are affected by stochastic noise, measurements can be described by a probability density function $p(y_k)$.

The goal of the tracking system 52 is to present the best description of $x_k$ given all measurements $\{y_j^i\}_{i=1, j=1}^{N,k}$ (for a system of N sensors), which is the conditional probability density function $p(x_k|y_1^1, y_1^2, \ldots, y_k^{N-1}, y_k^N)$.

When this distribution is known, an estimate $\hat{x}_k$ of the position of the object can be calculated. A very common estimator is to use the expected value $\hat{x}_k=E[x_k]$ Common tracking filters are the so called Kalman filter, e.g. with modifications such as the Extended Kalman filter or Unscented Kalman filter to handle nonlinearities, or Monte Carlo methods such as particle filters, which is a widely used filter based on Monte Carlo methods. A tracking system 52 uses process models and sensor models to calculate the result. The resulting track is a combination of all received data, and estimation errors are therefore correlated in time, although smaller than the measurement error.

The Kalman filter is an efficient recursive filter that estimates the state of a dynamic system from a series of incomplete and noisy measurements.

An example application of how to use an Kalman filter would be providing accurate continuously-updated information about the position $\hat{x}_k$ and velocity of an object given only a sequence of observations about its position $\hat{x}_k$, each of which includes some error. It is used in a wide range of engineering applications from radar to computer vision. Kalman filtering is an important topic in control theory and control systems engineering.

For example, in a radar application, where one is interested in tracking a target (also called object in this context), information about the location, speed, and acceleration of the target is measured with a great deal of corruption by noise at any time instant. The Kalman filter exploits the dynamics of the target, which govern its time evolution, to remove the effects of the noise and get a good estimate of the location of the target at the present time (filtering), at a future time (prediction), or at a time in the past (interpolation or smoothing). A simplified version of a Kalman filter is the alpha beta filter, still commonly used, which has static weighting constants instead of using co-variance matrices.

Figure 2:
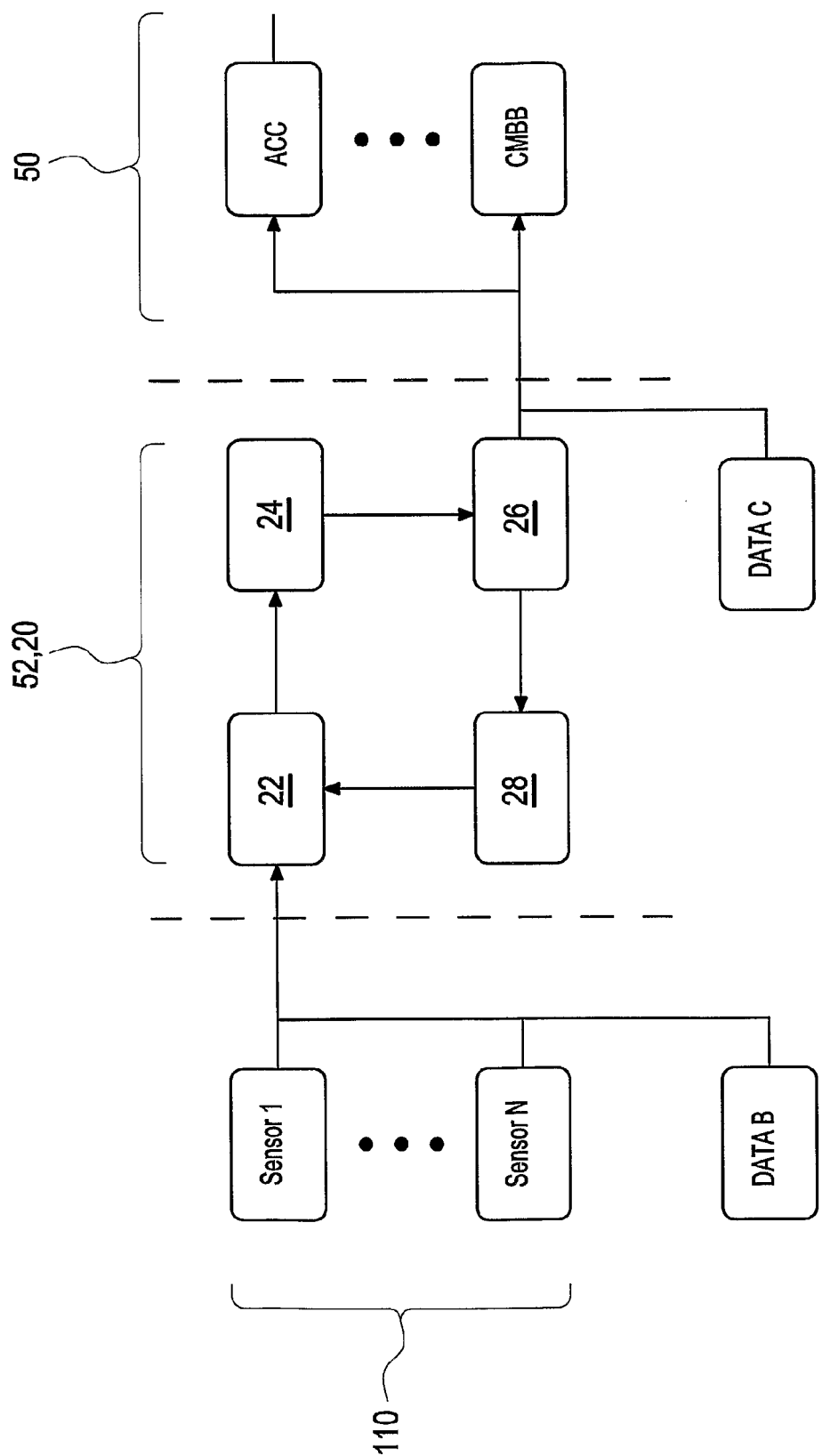
FIG. 2 a preferred tracking system which comprises also a sensor fusion system according to the invention.

FIG. 2 illustrates a preferred tracking system 52, which is also a sensor fusion system 20.

When there is a multitude of sensors 110, i.e. N>1, the tracking system 52 is also a fusion system 20, because it uses several data sources, i.e. sensor 1 to sensor N, to calculate the estimate of $x_k$. The sensor signals are fed into the fusion system 20, which, when embodied as tracking system 52 may comprise a unit 22 providing gating and data association, connected to a unit 24 which initiate new tracks, update track score and delete tracks (i.e. perform track management), which is connected to a unit 26, providing updated tracks to the receiving applications, which is connected to a unit 28, providing predictions such as position $\hat{x}_{k+1}$ being connected to unit 22 as the predicted starting point used by the system at the start of the next iteration to associate data with position and used in the next iteration of the tracking system 52. Particularly, the state space position is predicted using a motion model. This is needed to associate the updated track from the previous iteration with the measurements of the following iteration. As will be shown in FIG. 3 track-to-measurement association is assumed to be hard just when the two tracked vehicles are positioned close to each other.

The unit 26 outputs data to various applications 50 such as Active Cruise Control (ACC), Collision Mitigation by Braking (CMBB) and the like.

However, a fusion system 20 can be much more than just a tracking system 52 or an application 50. In fact, a fusion system 20 needs not to contain a tracking system 52. It can contain information fusion on "higher" algorithmic levels that a tracking system 52, or make use of situation assessment algorithms to "understand" e.g. the traffic situation, and the like. In some sense, any system that makes use of multiple sources of information can be said to perform sensor fusion at the widest sense of the concept.

The state vector $x_k$ is likely to contain the positions, velocities, accelerations and/or orientation of surrounding objects such as e.g. vehicles. A sequence of positions believed to originate from a single object is a so called "track".

For algorithmic efficiency, a "track" in a tracking system is sometimes simply the estimated position $\hat{x}_k$ of an object at time $t_k$. "Position" does not necessarily mean a two-dimensional (2D) position in Cartesian space, it depends on the parameterization of the object and it is common to be of higher dimensions. For example, the 6-dimensional "constant acceleration" representation is widely used in automotive tracking systems with coordinates $(x, y, \dot{x}, \dot{y}, \ddot{x}, \ddot{y})$, where x, y are orthogonal vectors spanning a two dimensional space and the dots represent the time derivative ($\dot{x}$ being a first derivative, $\ddot{x}$ being a second derivative etc.).

Figure 3:
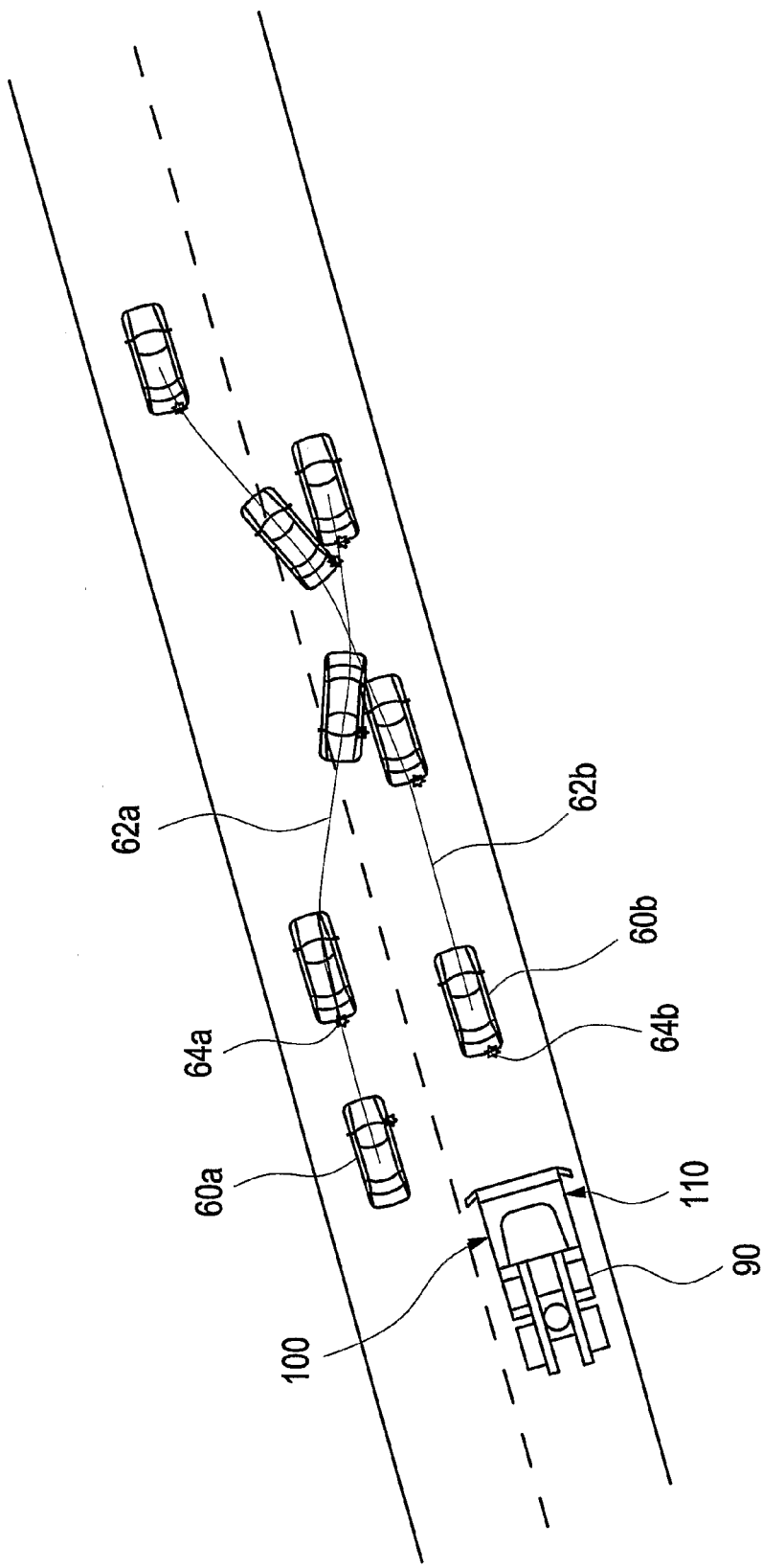
FIG. 3 an application of the invention when two vehicles moving ahead of a truck yielding one track per vehicle.

Referring now to FIG. 3 in order to illustrate the use of the invention in a preferred example embodiment, two vehicles 60a, 60b are moving ahead of a truck 90. The stars Ma, 64b assigned to the vehicles 6a, 60b (only one is referred to with a reference numeral for each vehicle 60a, 60b) can be associated to form two tracks 62a, 62b indicated by solid lines connecting the stars 62a, 62b, wherein track 62a is associated with the vehicle 60a and track 62b is associated with the vehicle 60b.

Typically, a tracking system (mounted e.g. on the truck 90) does not report a track 62a, 62b based in a single detection, but waits for several measurements to be associated before it is "sure enough". The result is the so called "validated track".

It is desired to minimize the time it takes to validate a track 62a, 62b, as it is not until it is validated that it can be safely used by an application 50 (e.g. collision mitigation). The more measurements received, the easier it is to validate or reject a track 62a, 62b. Preferably, the tracking system 52 will contain the invention leading to the reduced track validation time.

A "driver sensor", i.e. a sensor 100 which provides driver-related sensor data, can present estimates of driver head position (and/or another driver-specific position) and gaze direction. By way of example, the driver sensor 100 can be located in the truck 90. Through this driver sensor 100 it is possible to monitor the driver behaviour, which means that the driver is actually regarded as a sensor 100, the driver being monitored by the driver sensor 100. The other sensors 110, referred to as external sensors 110, typically detect positions and velocities of objects, such as the vehicles 60a, 60b, in the ambient of the truck 90. When the external sensors 110 and the driver sensor 100 are fused in the sensor fusion system (20 in FIG. 2), the track validation is facilitated and improves in performance and accurateness.

Referring back to FIG. 1, sensor data are collected by the driver sensor (100 in FIG. 3) and by at least one external sensor (110 in FIG. 3), e.g. a radar sensor 10 or the like monitoring the surrounding ambient 12. The driver sensor (100 in FIG. 3) and the at least one external sensor 100 are coupled to a tracking system 52, and are advantageously combined (fused) as the respective measurement errors of the data are uncorrelated in time with respect to the at least one application 50. The sensor data are combined as detections B, when the measurement errors are still uncorrelated in time at least with respect to their noise, and then treated in the sensor fusion system 20 (FIG. 2). The estimation error of the processed sensor data is correlated in time after processing in the sensor fusion system 20. After passing the fusion system the term "track" can be appropriately used for the sensor data, as most fusion systems consist of or comprise a tracking system. The sensor data (track) can subsequently be presented to an application 50.

As a benefit, it can also be compared how fast the two different sensor types, i.e. driver sensor 100 and external sensor 110, react with respect to the other. If the driver sensor 100 indicates a fast response or is even faster than the external sensor 110, it can be assumed that the driver is not distracted or drowsy. A change in such a relation can favourably be correlated with drowsiness, as the driver may become tired as time goes by, but the external sensors 110 are expected to perform the same all the time.

FIG. 4a to FIG. 4c illustrates a sequence of detection of an object. The object is by way of example a vehicle 60 moving on a driveway entering a road in which a truck 90 is moving.

In FIG. 4a, a truck-mounted sensor 110 detects the approaching vehicle 60 with a first detection at t=t0, indicated by star 64 attached to the vehicle 60 in the drawing. The stars 64 illustrate e.g. radar measurements. At this time, the object (vehicle 60) is hidden in the tracking system mounted on the truck 90. The approaching vehicle 60 may be still out of the field of view of the driver.

In FIG. 4b, at time t=t1, more detections have been made by the sensor 110 and the track of the object (vehicle 60) is validated, indicated by three stars 64 (illustrating radar measurements) attached to the vehicle 60, symbolizing the track. The tracking system reports the validated object (i.e. data C in FIG. 1. Before validation, data B may exist but data C is empty. When data B has proved the presence of an object (validation) it is reported as data C) which can then be used in vehicular functions such as collision warning, active cruise control, collision mitigation by braking or the like.

In FIG. 4c, at t=tD, a visual acknowledgement of the object 60 by a driver of the truck 90, i.e. by the driver sensor 100, is indicated. The vehicle 60 may just have entered the field of view of the driver and the driver may have looked at the spot where the vehicle 60 appeared. This may have been recognized by a driver-related sensor 100 by monitoring a change in the driver's glance direction and/or head position or the like.

Favourably, the time difference between the first detection at t=t0 and t=tD can be derived as a measure for the reaction time of the driver. Particularly, the driver helps validating the target as tD<t1.

Figure 4:
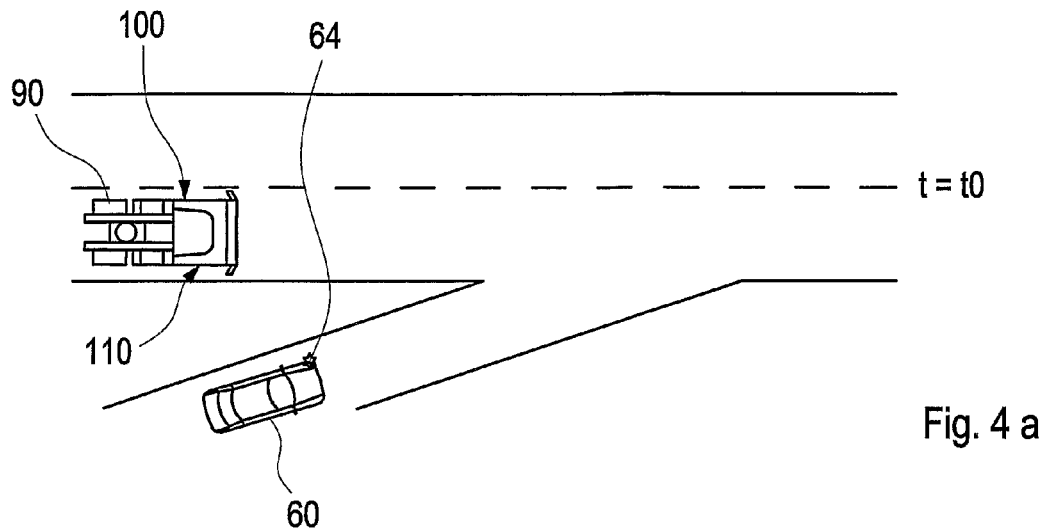
FIG. 4a-c a sequence of detection of an object with a first detection of the object hidden in a tracking system (FIG. 4a), reporting of the validated object (FIG. 4b) and visual acknowledgement of the object by a driver (FIG. 4c)
Figure 4:
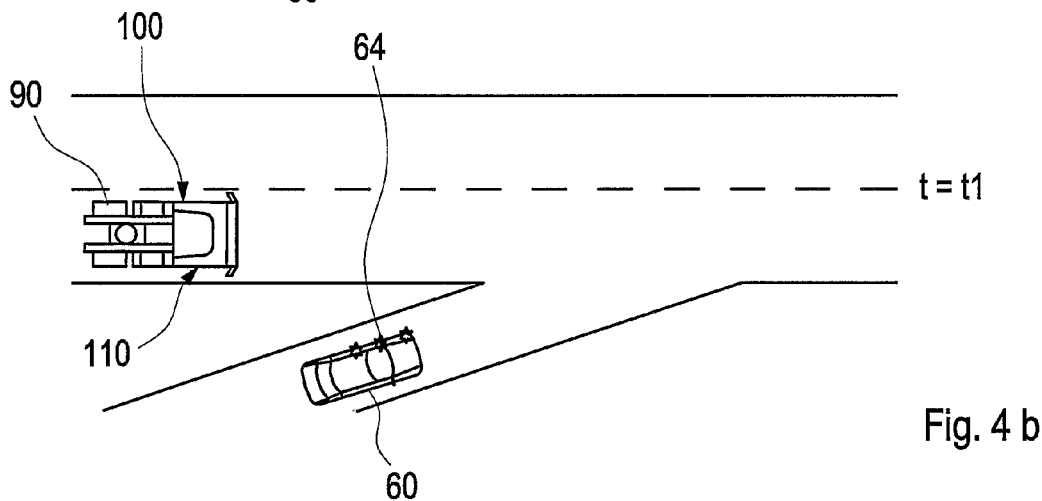
Figure 4:
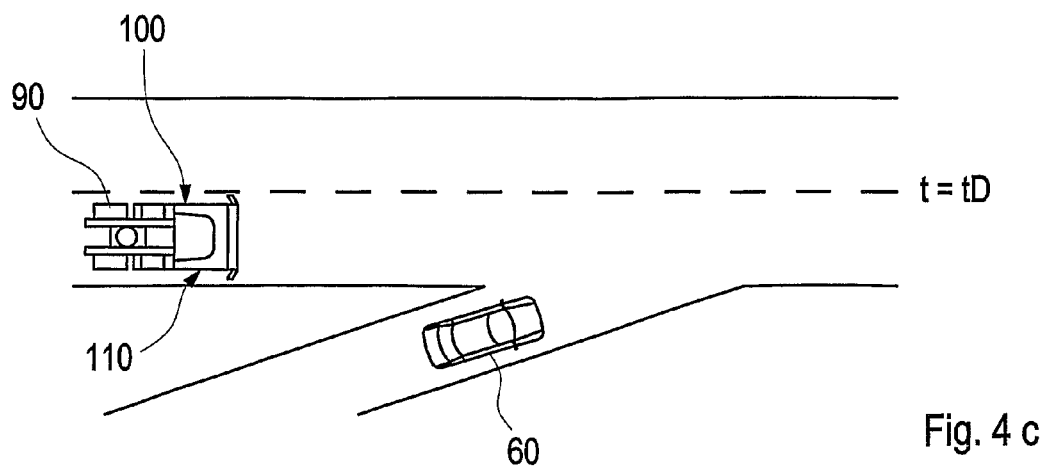
Figure 5:
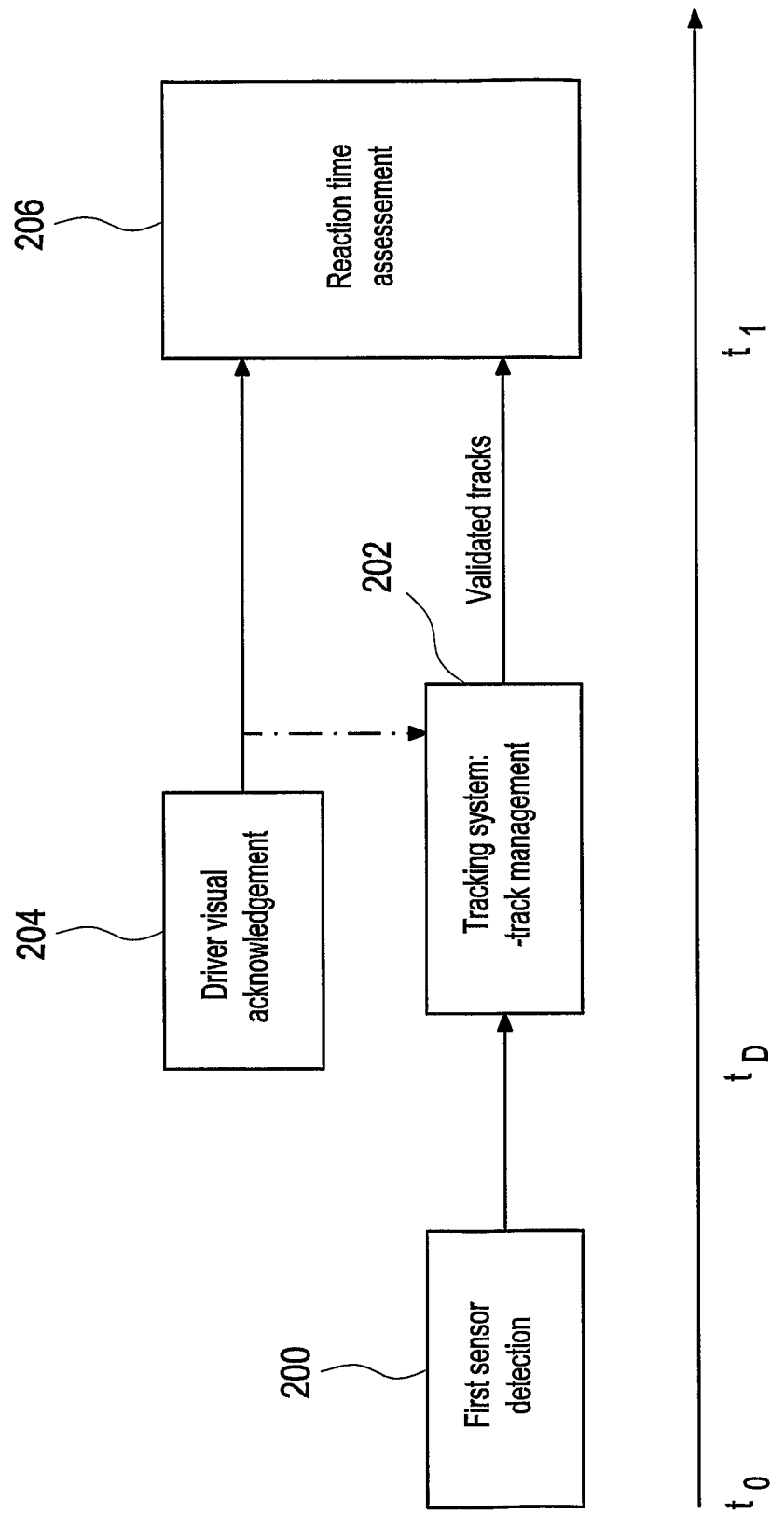
FIG. 5 a system description of a preferred tracking system.

FIG. 5 illustrates the sequence of FIG. 4 in a flow chart. At t=t0 a first sensor detection occurs in step 200. This first detection is entered into the tracking system in step 202 which performs track management and outputs validated tracks. The driver's visual acknowledges the object at t=tD in step 204. In step 206 a reaction time assessment is performed based on the time difference tD-t0.

If steps 204 and 202 are connected (indicated by a broken line), FIG. 4c illustrates both the calculation of a reaction time and a reduced track validation time, as in step 202 the track score part can be calculated.

The time it takes for the driver to react on the presence of detected objects (vehicle 60) can be used to estimate future reaction times, i.e. the time it takes from when a driving situation changes until the driver takes an appropriate action.

It is the mere presence of objects (e.g. vehicle 60) that will lead to some reaction from the driver in the truck. If the driver does not know of the vehicle 60 in the adjacent lane, the driver is likely to look towards it when seeing it in the "corner of his eye". This time tD can be assessed by measuring the time it takes for a driver to "visually acknowledge" an object (e.g. vehicle 60) from when a sensor first notices it at t=t0. In order to estimate this time, untracked (un-validated) sensor detections can be used as a time stamp for when the object (e.g. vehicle 60) first appears in the driver field of view. By using the track position that later will be reported as a base for the position, the time of the first track detection t0 can be subtracted from when the driver looks at that spot at tD, wherein for a typical radar sensor, "later" means a time less than a second, by way of example between 100 ms to 400 ms. This results in an estimate of the cognitive reaction time of the driver.

This is made possible by early information fusion at the level of sensor tracking algorithms, i.e. by considering the driver sensor and one or more external sensors. This is superior to known methods, as due to latencies in sensor systems and limited sensor coverage it is not sufficient to estimate such reaction times using tracks, which is what a sensor system supplies on a high level. A main reason is that the true track age, related to the occurrence of the very first detection, is unknown. It is known in the art to estimate the reaction time based on manoeuvres by already detected objects, but this provides a more subtle assessment and may be influenced by differences in driver behaviour.

The time t1-t0 is generally unknown because t1 is the only time stamp available. Then it will be impossible to derive the desired reaction time tD-t0. Because it is possible for tD to be smaller than t1, this is not even possible to calculate on a higher level. However, according to the invention, by altering the tracking the time stamp of the first detection can be included.

Favourably, a measurement can be derived that is likely to be correlated with the driver reaction time and distraction level. This can be done by looking not on how the driver handles the own vehicle, but rather how much better or worse the driver is at assessing the environment compared to a sensor system consisting of or comprising radars/lidars/cameras and the like.

Figure 6:
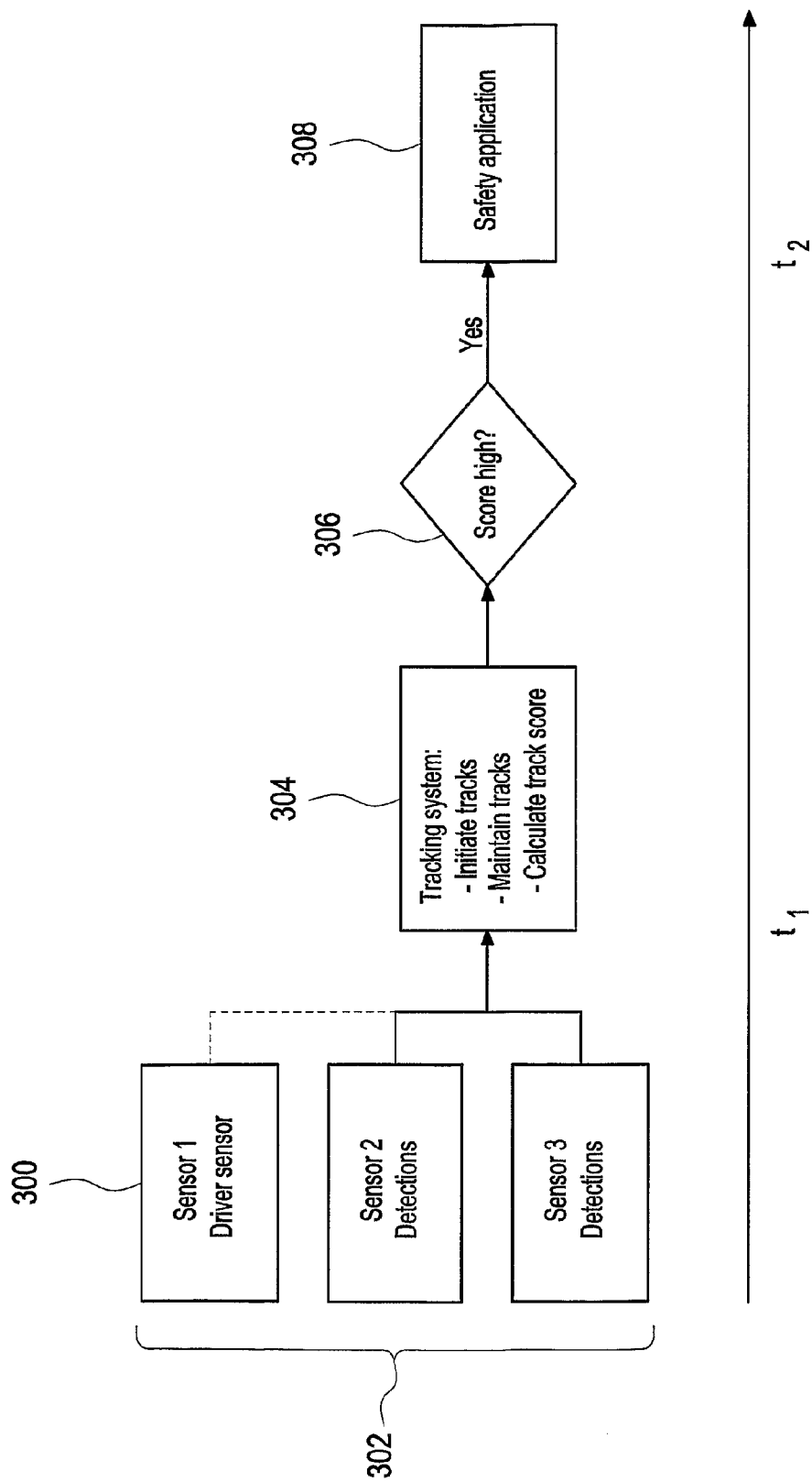
FIG. 6 a tracking system providing a functionality for "driver acknowledgement"

FIG. 6 displays a further preferred embodiment of the invention by depicting a tracking system providing a functionality for "driver acknowledgement".

The driver is an information provider and can favourably be modelled as a sensor additional to one or more external sensors which monitor the environment. If the driver looks quickly or often to some point there is a high probability that something is there, e.g. an approaching vehicle (object) or the like.

This can be used in early tracking, i.e. sensor fusion, to identify objects for example in cluttered environments, or to prepare a tracking system to see an object that may enter the field of view of a traditional sensor. The driver can be expected to have a wider field of view than a single sensor system.

FIG. 6 provides a schematic illustration of a tracking system with an additional functionality for "driver acknowledgment". Data of a multitude of sensors, i.e. sensor 1 (driver sensor) sensor 2 (detections), sensor 3 (detections) in step 302 are fed into a tracking system in step 304. The driver sensor may deliver a signal of a visual acknowledgment of an object. Whether the activity is a visual confirmation or not is preferably judged by the tracking system, comparing the visual activity with other sensor data. In step 306 it is checked if the tracking score is high. If yes, the object (e.g. vehicle 60 in FIG. 4a-4c) has been identified as a valid confirmed target to be reported to a safety application, e.g. a collision warning system.

The time t0 represents when a sensor first detects the presence of a probable object and t1 represents when the object has been identified as a valid confirmed target to be reported to the safety application. It is desirable that the time t1-t0 should be as small as possible.

By incorporating driver focus/attention as a sensor capable of generating measurements, new tracks can be quickly started, thus increasing the track score in order to gain higher confidence values. This is formally achieved by making a sensor model in the tracking theory sense, modelling (at least):
the probability that a driver notices an object (a function of the driver field of view),
(i) the accuracy of which the driver monitoring camera presents the head/gaze direction,
(ii) the relation between head/gaze direction and position of viewed objects
(iii) the probability that the driver looks at "non-objects"
(iv) the impact on track confidence as a function of driver awareness.

These quantities can all be theoretically and/or experimentally derived and the "driver sensor" can be handled similar to the way any (external) sensor is used in a sensor data fusion system.

This can of course also be used for threat assessment. For instance, it is reasonable to regard a track that has not been visually acknowledged by the driver for some time, as a larger threat than a track that the driver looked at recently.

By introducing visual acknowledgement of targets, a preferred safety system can perform better and act quicker. It is also possible to provide information to a system whether a driver is aware of a particular target or not.

It should be noted that, if the "reduce validation time" option in FIG. 4c is active (box 204 connected to box 202), box 202 is equal to box 304.

Figure 7:
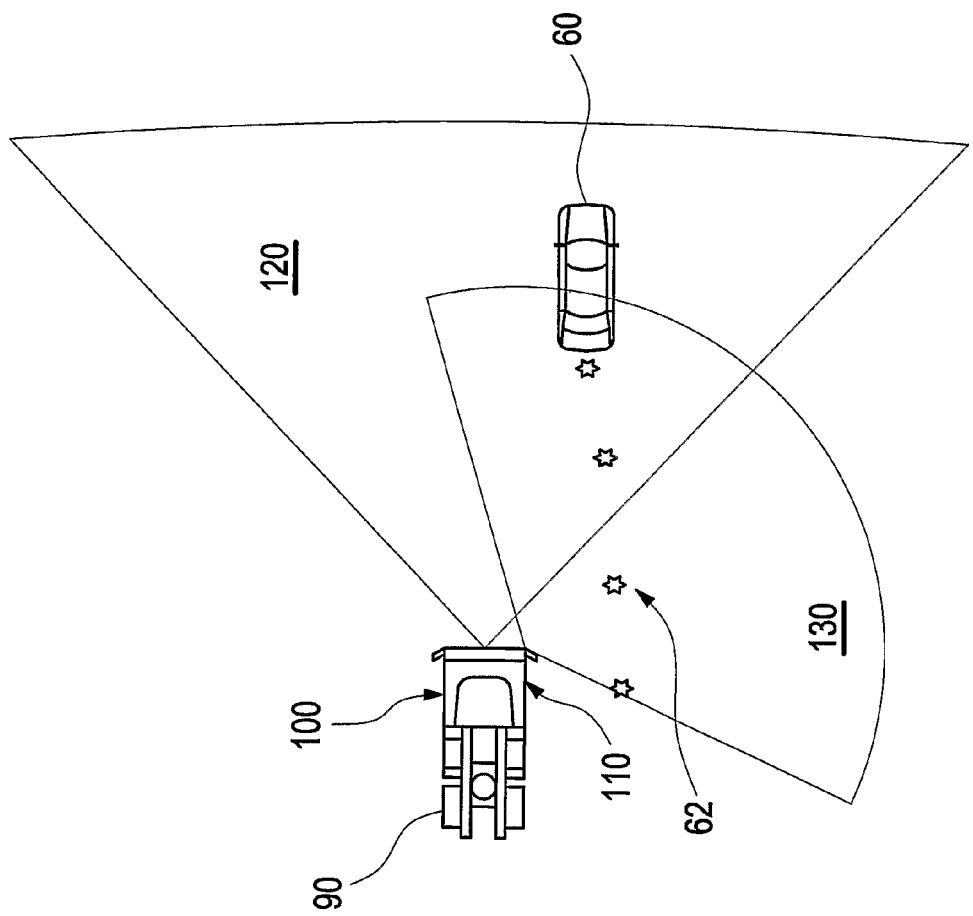
FIG. 7 an example where an obstacle is first detected by an external sensor field and validation is not influenced by a driver sensor at this first stage.

FIG. 7 illustrates an example where an object, e.g. a vehicle 60, is first detected by an external sensor 110 mounted on a truck 90 and validation of the detection is not influenced by a driver sensor 100 at this first stage. At a later stage, when the object and/or its track 62 may be already validated, the driver sensor 100 may influence the validation. A sensor field of view 130 is assigned to the external sensor 110 wherein the object (vehicle 60) enters the external sensor field 130. A field of view 120 is assigned to the driver of the truck 90. It can be estimated how long it takes for the driver to visually acknowledge the vehicle 60, i.e. the track 62 assigned to the vehicle 60, after entering the driver's field of view 120, as long as it is known for the low level fusion or tracking when the track 62 entered the field of view 120.

Favourably, this setup can be used to estimate the region in which the driver can see objects, in other words estimate the driver visual field of view 120. This is done by remembering where objects usually are when visually acknowledged by the driver sensor 100. After some time the region will be known and assigned as the driver's field of view 120. This can be used by threat assessment algorithms that now can assess if a potential danger can be detected by the driver or not.

FIG. 8 illustrates an example where an object, e.g. a vehicle 60, is first detected by the driver sensor 100 and validation is not influenced by the external sensor 110 at this first stage. It is unlikely that the driver sensor 100 alone can validate a track 62 of the object (vehicle 60), being most probably a very noisy signal, but there is a reasonable probability that the presence for the track 62 can be quickly initiated when external sensor measurements are available. If the driver sensor 100 is present, this can advantageously be quicker than if the driver sensor 110 were not present.

It can be shown that if the vehicle 60 enters the two fields 120 and 130 at the same time, the effect would be that the two sensors (external sensor 110 and driver sensor 100) report the object presence at the same time, speeding up the validation time in a favourable manner.

If the driver is regarded as a driver sensor 100, it is necessary or desirable to describe what the driver sensor 100 is likely to measure at any given situation, that is to form a probability density $p(y_k|x_k)$ where y is the output of the sensor. Any function that has the capability of comparing two hypotheses with respect to data will function in this sense, even if the name "probability density" is not actually used.

A simple model can be the built with the probability $P_d$ (probability of detection), wherein the driver looks at a point close to the object with the probability $P_d$. This can be written, using $y=[\xi_x \xi_y]$: with probability $P_d$, the measurement will be $[\xi_x \xi_y]^T = [xy]^T + [v_x v_y]^T$, wherein $\xi_x$, $\xi_y$ is the position the sensor reports that the driver looks at, (x, y) is the position of an object and $v_x$, $v_y$ is stochastic noise that explains why the driver does not look exactly at the right spot, i.e. the actual measurement has two components, the actual position (signal) and the error (noise). For example, $v_x$, $v_y$ can be modelled as Gaussian random noise.

Extension of this model can include modelling the noise and the probability $P_d$ to be different if an object, e.g. another vehicle, is far away or seen through e.g. a rearward mirror. The class of the object, e.g. car, truck, pedestrian, road sign, intersection, can be used to affect noise and the probability $P_d$. Particularly, this can be employed if the external sensor 110 is a GPS system (GPS=Global positioning sensor) with a map database.

Noise can have other distributions, $P_d$ can be a function of $x_k$. Further the driver sensor measurement space may have more than two dimensions, measurement noise may not be additive, as it may enter through a more complex model, and the threat assessment by the driver may affect what object the driver chooses to look at.

The invention can be embodied as hardware or software or comprise both software and hardware. Further, the invention can be embodied as a computer program product which can be accessed from a medium which can be used or read by a computer. Preferably, the medium can provide a program code which can be used in a computer. Particularly, the medium can be a memory, such as a solid state memory, a RAM or a ROM and the like, a magnetic tape, a computer diskette, a magnetic or optical disc, a CD, a DVD, a USB stick etc.

The invention claimed is:

1. A method for combining sensor data collected by at least two sensors coupled to at least one application, comprising monitoring, using at least one of the at least two sensors, driver behaviour and providing driver-related sensor data of the driver-related behaviour, monitoring, using at least one external sensor of the at least two sensors that is not monitoring the driver behaviour and providing sensor data not related to driver-related behaviour, feeding sensor data of the at least two sensors to a sensor fusion unit and combining and/or exchanging the sensor data of the at least two sensors in the fusion unit when respective measurement errors of the data are uncorrelated in time and to each other and transmitting the sensor data to one or more applications subsequent to the sensor fusion unit, and correlating in time estimation errors after processing in the sensor fusion unit.

2. The method according to claim 1, wherein the sensor data are pre-processed before fed into the sensor fusion unit.

3. The method according to claim 1, wherein driver-related sensor data. comprises at least driver attention and/or driver gaze direction data.

4. The method according to claim 1, wherein the driver-related sensor data and data derived from the application are used to estimate the driver's field of view.

5. The method according to claim 1, wherein a reaction time of the driver and/or a distraction level of the driver is derived from a comparison between driver-related sensor data indicating cognitive detection of an object and detection of the object by the at least one external sensor.

6. The method according to claim 1, wherein a reaction time is extracted from a time difference between a detection of an object by the at least one external sensor and driver-related sensor data indicating cognitive detection of the same object (60) by the driver.

7. The method according to claim 6, wherein the at least one application is a vehicular safety system and the reaction time of one or more drivers is extracted and stored for use in the vehicular safety system.

8. The method according to claim 6, wherein the reaction time is used to adapt a sensitivity level of the safety system, and/or the reaction time is used to evaluate a level of driver attention.

9. The method according to claim 1, wherein the at least one application is a vehicular safety system.

10. The method according to claim 1, wherein the driver-related sensor data are combined with tracking data of one or more objects, wherein in a tracking system a sensor model is built which at least comprises one or more of a probability that the driver notices one or more object;

an accuracy of a driver monitoring camera presenting a driver's head and/or gaze direction;

a relation between head/gaze direction and position of one or more objects (60) viewed by the driver;

a probability that the driver looks at non-objects;

an impact on track confidence as a function of driver attention.

11. The method according to claim 10, wherein a track is recognized as valid if eternal sensor data and driver-related sensor data coincide.

12. A safety system of a vehicle employing the method according to claim 1.

13. A tracking system of a vehicle employing the method according to claim 1.

14. Computer comprising a. computer program code adapted to perform a method or for use in a method according to claim 1.

15. Computer program product stored on a non-transitory computer readable medium, comprising a program code for use in a method according to claim 1.

* * * * *